United States Patent [19]

Fulmer et al.

[11] Patent Number: 5,510,543
[45] Date of Patent: Apr. 23, 1996

[54] REMOVAL AND NEUTRALIZATION OF ACID CATALYST FROM PRODUCTS OF CUMENE HYDROPEROXIDE CLEAVAGE

[75] Inventors: John W. Fulmer, Mt. Vernon, Ind.; Andrei K. Griaznov, St. Petersburg, Russian Federation; William D. Kight, Poseyville; Vladimir M. Zakoshansky, Mt. Vernon, both of Ind.

[73] Assignee: General Electric Company, Pittsfield, Mass.

[21] Appl. No.: 353,004

[22] Filed: Dec. 9, 1994

[51] Int. Cl.$^6$ .................................................. C07C 37/68
[52] U.S. Cl. ........................... 568/754; 568/741; 568/742; 568/748; 568/749; 568/798
[58] Field of Search ...................... 568/798, 754, 568/749, 748, 741, 742, 768

[56] References Cited

U.S. PATENT DOCUMENTS

| | | | |
|---|---|---|---|
| 2,737,480 | 3/1956 | Adams | 568/798 |
| 3,931,339 | 1/1976 | Cooke | 568/798 |
| 4,016,213 | 4/1977 | Yeh et al. | 568/754 |
| 4,173,587 | 11/1979 | Wu et al. | 568/798 |
| 4,207,264 | 6/1980 | Anderson et al. | 568/798 |
| 4,262,150 | 4/1981 | Pujado | 568/754 |
| 4,262,151 | 4/1981 | Pujado | 568/754 |
| 4,310,712 | 1/1982 | Langley | 568/798 |
| 4,355,190 | 10/1982 | Nambu et al. | 568/754 |
| 4,358,618 | 11/1982 | Sifniades et al. | 568/798 |
| 4,370,205 | 1/1983 | Pujado | 568/754 |
| 4,929,786 | 5/1990 | Himmele et al. | 585/469 |
| 5,015,786 | 5/1991 | Araki et al. | 568/798 |
| 5,017,729 | 5/1991 | Fukuhara et al. | 568/798 |
| 5,144,094 | 9/1992 | Richmond et al. | 568/798 |
| 5,254,751 | 10/1993 | Zakoshansky | 568/798 |
| 5,304,684 | 4/1994 | Nishida et al. | |
| 5,371,305 | 12/1994 | Hood | 568/798 |

FOREIGN PATENT DOCUMENTS 7080332  11/1980  Japan.

OTHER PUBLICATIONS

"Side Reactions in the Phenol/Acetone Process. A Kinetic Study" Ind. Eng. Chem. Res. 1988, 27, 4–7–Pier Luigi Beltrame, Paolo Carniti, Aldo Gamba, Oscar Cappellazzo, Loreno Lorenzoni and Giuseppe Messina.

Primary Examiner—Werren B. Lone

[57] ABSTRACT

The present invention is an improved method for the recovery of phenol from a cleavage mass resulting from the sulfuric acid cleavage of cumene hydroperoxide comprising neutralizing the cleavage mass, forming an aqueous phase and an organic phase, separating the organic phase into an acetone-rich stream and a phenol-rich stream, removing phenol tars from the phenol-rich stream and cracking the phenol tars wherein the improvement comprises maintaining the pH of the cleavage mass during neutralization between 4.0 and about 4.9 whereby the sulfuric acid is converted to the bisulfate salt and substantially no free sulfuric acid remains in the cleavage mass and corrosion of process equipment is reduced.

As a result of this improved process, a phenol tar waste stream containing less than about 4 parts per million by weight of chromium is obtained.

9 Claims, 1 Drawing Sheet

REMOVAL AND NEUTRALIZATION OF
ACID CATALYST FROM PRODUCTS OF
CUMENE HYDROPEROXIDE CLEAVAGE

The present invention relates generally to a process for the production of phenol by the oxidation of cumene and mineral acid-catalyzed cleavage of cumene hydroperoxide. In particular it relates to the removal and neutralization of mineral acid catalyst and by-product organic acids from the cleavage products.

The production of phenol by the oxidation of cumene followed by the mineral acid-catalyzed cleavage of cumene hydroperoxide is well-known. The cleavage product contains phenol and acetone as the principal products together with varying amounts of side-products in the form of tars and organic substances such as organic acids. Before the products can be recovered it is necessary to remove or neutralize the mineral acid catalyst in the cleavage products since the presence of the acid catalyst in the subsequent distillation interferes with the efficient recovery of the products and by-products of the reaction in addition to causing corrosion of the distillation equipment. Such neutralization is accomplished by adding sodium hydroxide or other suitable alkali metal hydroxide or oxide to the cleavage product mixture. Two immiscible phases are formed. The top organic phase is the neutralized cleavage mass and the bottom aqueous phase is the resulting sodium sulfate, or alkali metal sulfate, solution (higher density). Good separation of the aqueous phase from the organic phase is essential before the organic phase is subjected to downstream distillation.

It is taught in U.S. Pat. No. 3,931,339 to contact the products of the mineral acid catalyzed cleavage of cumene hydroperoxide in a first zone with an aqueous solution comprising an inorganic salt and an excess of an alkali metal hydroxide or alkali metal phenate over the stoichiometric quantity required for neutralization of the mineral acid catalyst and organic acid by-products. The described invention employing an excess of alkali metal hydroxide or alkali metal phenate to completely remove the mineral acid catalyst and at least part of the organic acids present as alkali metal salts is asserted to overcome the disadvantages of the prior art which attempted to maintain the pH slightly below 7.0 during the catalyst removal and neutralization step in order to prevent alkali metal phenate being carried over to the subsequent washing step.

It is further taught in '339 that difficulties are experienced during commercial operation in maintaining the pH slightly below 7.0 resulting in the aforementioned disadvantages. Moreover even if the pH is successfully maintained below 7.0 it is sometimes found that chemical losses, e.g. loss of methylstyrene, occur under acid conditions.

The pH is preferably maintained by the '339 patented invention in the range of 7 to 9 to overcome these prior art problems and to minimize corrosion of downstream equipment which occurs when the acids are not completely neutralized.

Phenol is itself acidic and will convert to its alkali metal salt above a pH of 6.5 resulting in an undesirable yield loss. The phenate salt, once formed, is soluble in the organic layer and carries through in the organic phase to downstream equipment fouling reboilers and contamination of tars which must be incinerated or otherwise disposed of in an environmentally sound manner.

U.S. Pat. No. 4,262,150 teaches a different process to recover phenol from the reaction mixture resulting from the acid cleavage of cumene hydroperoxide. It broadly embodies effecting the neutralization of the reaction mixture, and forming a reaction mixture comprising a phenol, a ketone, a secondary alkylbenzene and a salt of neutralization; (b) processing an initially salt-free aqueous stream in counter current contact with the neutralized salt-containing reaction mixture; (c) progressively saturating the resulting aqueous phase with said salt, and salting out the organic acid cleavage products contained therein whereby the aqueous phase is recovered containing substantially all of said the and substantially free of organic products.

One of the more specific embodiments of the '150 invention is a method for treating a reaction mixture resulting from the sulfuric acid cleavage of cumene hydroperoxide comprising the steps of (a) effecting the neutralization of the reaction mixture with sodium phenate, and forming a reaction mixture comprising phenol, acetone, cumene and a sodium sulfate salt of neutralization; (b) processing an initially salt-free aqueous stream in counter current contact with the neutralized sodium sulfate-containing reaction mixture at a temperature of from about 95° to about 120° F. and at a pH of from about 2 to about 6; (c) progressively saturating the resulting aqueous phase with the sodium sulfate and salting-out the organic acid cleavage products contained therein whereby the aqueous phase is recovered containing substantially all of the sodium sulfate and substantially free of organic products.

The process disclosed in the '150 patent is complex with repetitive cycles requiring substantial energy input and capital investment.

A simpler, more controllable process is now required to meet environmental concerns at a reasonable level of investment.

U.S. Pat. No. 4,262,151 describes an even more convoluted approach to solving this critical problem which comprises (a) effecting the direct neutralization of the acid cleavage reaction mixture and forming a reaction mixture comprising a phenol, a ketone, a secondary alkylbenzene and a salt of neutralization; (b) charging the salt-containing reaction mixture to the mixing stage of the first of a plurality of mixer-settler means, and admixing the same therein with a salt-containing aqueous phase charged to a mixing stage in accordance with step (g); (c) separating an organic phase and an aqueous phase in the settling stage of the first mixer-settler means; (d) charging the organic phase to the mixing stage of each succeeding mixer-settler means from the settling stage of the next preceding mixer-settler means and effecting a progressive decrease in the salt concentration of the organic phase in contact with an aqueous phase charged to the mixing stage in accordance with step (g); (e) charging a substantially salt-free water stream to the mixing stage of the last of the plurality of mixer-settler means, and admixing the same therein with an organic phase charged to the mixing stage in accordance with step (d); (f) separating an organic phase and an aqueous phase in the settling of stage of the last mixer-settler means; (g) charging the aqueous phase to the mixing stage of each preceding mixer-settler means from the settling steps of the next succeeding mixer-settler means, and effecting a progressive increase in the salt concentration of the aqueous phase in contact with an organic phase charged to the mixing stage in accordance with step (d); (h) discharging the salt-containing aqueous phase from the settling stage of the first mixer-settler means substantially free of the organic phase; and (i) recovering a substantially salt-free organic phase comprising a phenol, a ketone and unreacted alkyl-substituted aromatic hydrocarbon from the settling stage of the last mixer-settler means.

In the process of the '151 patent a sodium sulfate-containing reaction mixture is charged to the mixing stage of the first mixer-settler means and mixed at a temperature of from about 95° to about 120° F. and at a pH of from abut 2 to about 4 with a sodium sulfate-containing aqueous phase as in steps (e),(f) and (g) of the disclosed process. Not only is this process complex and capital intensive, it is very difficult to control pH in the highly acidic pH range of 2 to 4. Process reliability, is extremely difficult if a key parameter such as pH is not controlled. Further, in the pH range of 2 to 4, sulfuric acid exists in the free state and if it passes downstream in this form, it will cause heavy corrosion which will severely damage the process equipment and could cause material spills and environmental and safety hazards.

It has now been discovered that a partial neutralization of the sulfuric acid, employed as a catalyst in the cleavage of cumene hydroperoxide, to its half neutral salt, sodium hydrogen sulfate, i.e. sodium bisulfate ($NaHSO_4$), results in improved phenol yields, prevention of downstream equipment corrosion and minimization of ash content in phenol tars. This partial neutralization is accomplished by controlling the level of sodium hydroxide, or other suitable alkali metal hydroxide or oxide added to neutralize the cleavage mass, i.e., the product of cumene hydroperoxide cleavage, to control the pH of the aqueous phase during neutralization to the range of from about 4.0, to about 4.9. Within this pH range the sulfuric acid is converted to $NaHSO_4$, not $Na_2SO_4$, substantially no free $H_2SO_4$ exists and only a small portion of the organic acids are converted to their basic salts with a major portion of the organic acids remaining in the free, un-neutralized state. The substantial absence of free $H_2SO_4$ and the reduction in the level of organic acids converted to salts results in a surprising reduction in corrosion of downstream equipment.

It has been determined that the sodium salts of the organic acids are non-volatile and do not distill overhead during the subsequent distillation processes. Instead they pass to the bottoms of the columns during distillation and concentrate to high levels in the sumps of the hot distillation columns where they then decompose due to the heat and revert to their free acid state. Once formed in this severe environment, these acids quickly corrode the stainless steel equipment, causing severe damage, and leaching out of chromium, nickel and iron, which is environmentally undesirable since this metal contamination ultimately finds its way into the phenolic tar, which must be properly disposed of or burned in governmental regulated incinerators. Is Thus complete neutralization as taught by the prior art, only increases corrosion while partial neutralization with control of pH between 4.0 to 4.9 preferably about 4.0 to about 4.7 more preferably about 4.0 to about 4.5, and most preferably 4.0 to about 4.2 substantially reduces corrosion.

In a preferred embodiment, only about 60%, preferably less than 50% and more preferably less than 40%, by weight of the organic acids are converted to their sodium salts during neutralization. Thus a substantial portion of these acids are allowed to remain in their free acidic state so that they exist as low-boiling volatile, distillable compounds during subsequent downstream distillation. In this manner they can be quickly removed as an overhead distillate cut and not allowed to build-up in concentration or find their way to the hot sumps of the columns. Corrosion in the top of the column is minimal because temperatures are lower and the organic acids are quickly purged from the columns.

Once the organic acids are separated from the phenol containing product stream, the acids can be treated with sodium hydroxide to fully neutralize them preferably at a pH of up to 9 or above. Since there is no phenol present, any suitable high pH can now be employed. The organic acid salts are ultimately purged from the process in a waste water stream.

As a result of the reduced corrosion in the downstream equipment, which prolongs equipment life, the process of the present invention also reduces the level of metals contamination in the phenol tar waste stream which is disposed of in accordance with government regulations as a hazardous waste. The reduction in chromium content in this stream is particularly beneficial in reducing the environmental impact of disposition of this waste stream. Chromium is one of the elements in the stainless steel alloy employed in downstream equipment. The usual method of disposition of this tar stream is by incineration.

In a preferred embodiment of the present invention, an amount of aromatic hydrocarbon effective to facilitate phase separation is added to the input to the neutralization step. Preferred aromatic hydrocarbons are those obtained as by-products of the phenol from cumene process or inputs to the phenol from cumene process. More preferred aromatic hydrocarbons are alkyl or alkenyl benzenes. Most preferred are cumene, alpha-methylstyrene or a mixture thereof. Any and all of these compositions may be found in the recycle streams of the phenol process. The aromatic hydrocarbons which are water immiscible are added in an amount of from about 3 to about 15 percent by weight of the total input stream, preferably from about 4 to about 12 weight percent and most preferably from about 5 to about 10 weight percent. The improved phase separation reduces sodium salt entrainment. Reduced sodium salt entrainment reduces heat exchanger fouling and further reduces corrosion. Fouled heat exchangers cause process downtime and loss of production. Entrained salts end up in the phenol tar stream and complicate the disposal of these tars by incineration in compliance with government environmental regulations. Thus, the improved phase separation resulting from this embodiment of the invention reduces a major cause of process downtime, fouled heat exchangers, and lessens the environmental impact of waste phenol tar disposal.

BRIEF DESCRIPTION OF DRAWING

Turning now to FIG. 1, vessel (1) represents the cumene hydroperoxide cleavage stage of the process from which the cleavage mass containing residual sulfuric acid catalyst enters the neutralizer (2) through line (3). The pH of the neutralizer (2) is carefully controlled between 4.0 and 4.9, preferably between 4.0 and about 4.7 and more preferably between 4.0 and about 4.5 and most preferably from 4.0 to about 4.2, so that the residual sulfuric acid catalyst is converted primarily to $NaHSO_4$, preferably at least about 99 percent by weight of sulfuric acid is converted to $NaHSO_4$, more preferably about 99.9 percent by weight and most preferably about 99.99 percent by weight. In this pH range substantially no free sulfuric acid remains. A pH of about 4.1 is the target pH for optimum process operation.

Figure 1:
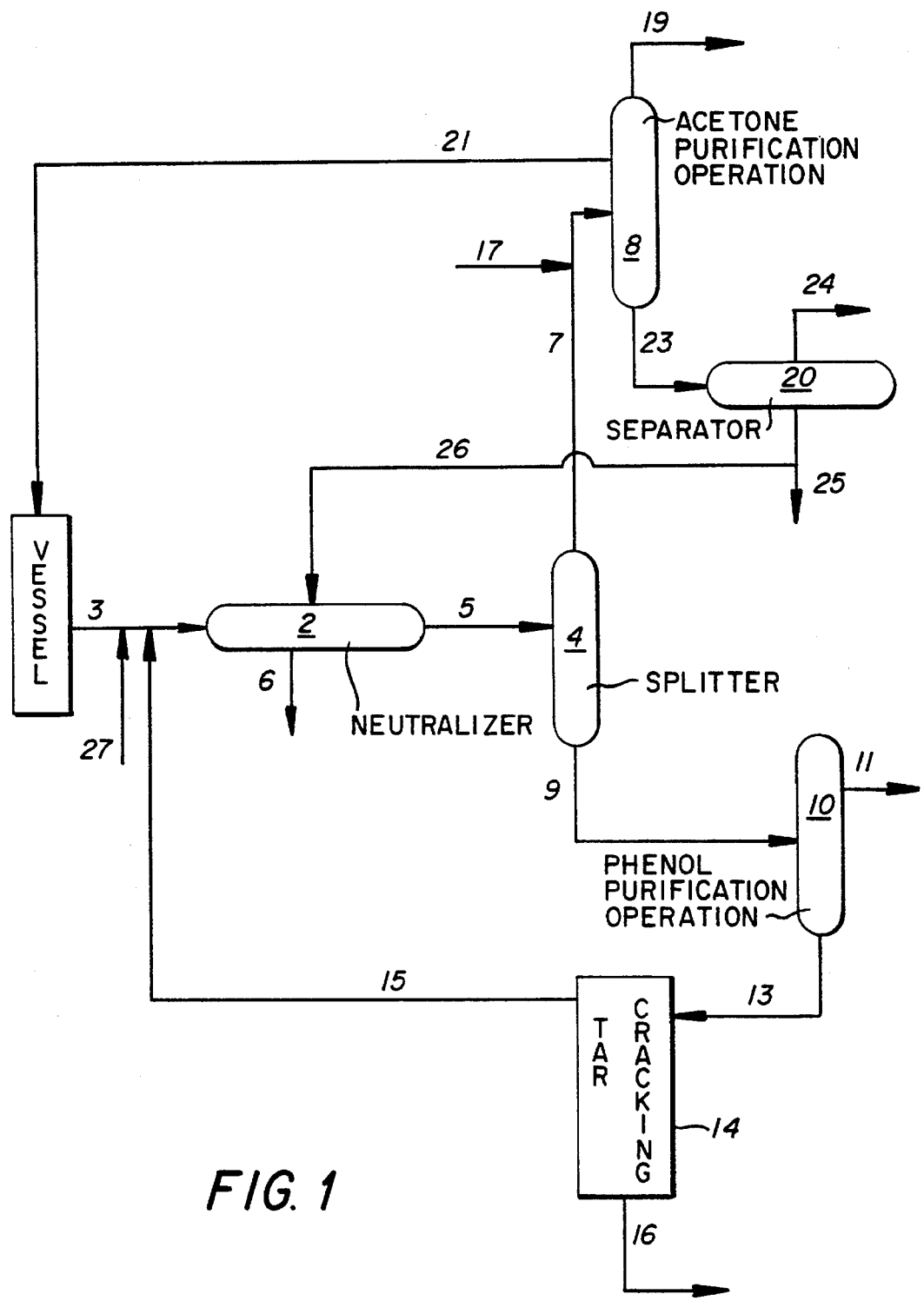
FIG. 1 is a process flow diagram of that portion of the process for the production of phenol and acetone from cumene which employs the improvements of the present invention.

Two phases, organic and aqueous, are formed in the neutralizer (2). The organic phase leaves the neutralizer (2) and enters the splitter (4) through line (5) with the aqueous phase containing sulfates leaving the neutralizer (2) through line (6). Although substantially all of the aqueous phase exits the neutralizer (2) through line (6) a small amount of water in minuscule droplets is entrained in the organic phase leaving the neutralizer in line (5). This entrained water is visible as a faint haze in the organic phase and contains a high level of salts, including sodium bisulfate and sodium salts of the organic acids. Elimination of this entrained salt-containing water before it enters the splitter (4) has a marked effect on the level of sodium salts corrosion in the splitter and downstream equipment. Installation of a coalescer in line (5) is a most effective way to reduce this minor amount of aqueous solution of these various salts substantially and further reduce the corrosion in the bottom of the splitter and other downstream equipment. The sodium levels in lines (9) and (5) as set forth in the examples were measured with the coalescer in operation. The sample point in line (5) was between the coalescer, not shown in the drawing, and the splitter (4). The splitter is a distillation column. The organic phase is separated in the splitter (4) with the acetone-rich portion containing the organic acids exiting overhead through line (7) and the phenol-rich portion containing the tars exiting as bottoms through line (9). Prior to the present invention the bottom portion of the splitter (4) was subject to severe corrosion from the organic acid salts which are soluble in the organic phase and which, when subjected to the high temperatures in the bottom portion of the splitter (4) reformed as acids causing heavy damage and requiring frequent repairs to, and replacement of, splitter (4). The phenol-rich portion is purified and treated in the phenol purification operation (10) from which phenol product is taken through line (11) to storage or use and tars and heavy ends are taken through line (13) to tar cracking (14). In tar cracking (14) usable products are recycled through line (15) to the neutralizer (2) and waste tars and residual salts are taken to waste disposal through line (16). It is in the disposition of these waste tars and residual salts where the environmental benefit of the low corrosion in the splitter (4) is found. The reduction in the level of chromium ions in the stream in line (16) lessens the level of hazardous waste products from the incineration or other disposal of this stream reducing the environmental impact of such waste disposition. The overhead from the splitter (4) is taken to the acetone purification operation (18) through line (7). As noted above, this overhead stream in line (7) contains the organic acids remaining from the neutralization according to the process of the present invention in neutralizer (2). Before the stream enters the acetone purification operation (18), sodium hydroxide, or other suitable alkali metal hydroxide or oxide, preferably as an aqueous solution, in an amount sufficient to neutralize all of the organic acids in the stream, e.g., preferably to raise the pH of the stream to about 9 is added through line (17). Acetone product is taken through line (19) to storage or use. Recycle acetone may optionally be returned through line (21) to the cumene hydroperoxide cleavage stage of the process (1) but such recycle through line (21) may, under some circumstances, not be the preferred method of process operation. The heavy organics including cumene and the aqueous phase containing acid salts are taken to a separator (20) through line (23). The separator separates the organic phase from the aqueous phase with the organic phase taken to a cumene recovery operation through line (24) and the aqueous phase being split between waste water containing the organic acid salts being taken to waste disposal through line (25) and recycle alkaline water returned to the neutralizer (2) through line (26). Because of the high pH of the recycle alkaline water returned to the neutralizer (2) through line (26), it is necessary from time to time to actually add sulfuric acid into line (3), to the neutralizer (2) to keep the pH of the neutralizer (2) within the 4.0 to about 4.9 range. The key is to monitor the pH of the cumene hydroperoxide cleavage mass (1) and the recycle alkaline water in line (26) and add sufficient acid into line (3) to the neutralizer (2) to keep the pH of the neutralizer (2) in the 4.0 to about 4.9 range.

Example 1 and Comparative Examples 1A and 1B

Except as set forth in the following description of these examples the phenol process was operated under standard operating conditions as known to the skilled phenol artisan. For periods of one month or more, the pH of the neutralizer (2) was controlled within the ranges set forth in Table 1 by monitoring the pH level of the recycle alkaline water and adding minor amounts of sulfuric acid to the neutralizer (2) through line (27) and line (3) when the acidity of cumene hydroperoxide cleavage (1) was running on the high side of the pH range. The composition of the bottoms stream in line (9) from splitter (4) was monitored for the weight content of chromium, sodium and total solids with the range of results as shown in Table 1:

TABLE 1

|  | Example 1 | Comparative 1A | Examples 1B |
|---|---|---|---|
| Neutralizer (2) pH | 4.2–4.7 | 6.0–6.5 | 3.8–3.9 |
| Analysis of Bottoms Stream in line (9) |  |  |  |
| Chromium (parts per million) | 0.05–0.10 | 0.5–1.5 | 0.7–2.2 |
| Sodium (parts per million) | 30–60 | 80–100 | 30–50 |
| Total Solids (parts per million) | 90–100 | 250–350 | 80–90 |

The level of sodium in process stream in line (9) stream, which indicates the level of sodium salts in the stream, as set forth in Table 1 is proportional to the amount of sodium hydroxide added to neutralizer (2), i.e., the less sodium hydroxide added to neutralizer (2) the lower the pH of neutralizer (2) and the lower the level of sodium in the line (9) stream. Total solids is the total ash content of the line (9) stream which includes the sodium salts not exiting the neutralizer (2) through line (6). The key parameter is the chromium level in the line (9) stream. The chromium level shows the extent of corrosion of the stainless steel internals of splitter (4). Below the pH range of 4.2 to 4.7, the level of corrosion is from about 7 to about 20 times greater than within this range. Above the pH range of 4.2 to 4.7, the level of corrosion is from about 5 to about 15 times greater. The explanation for this minimum corrosion level in the 4.0 to 4.9 pH range is given above, i.e., the conversion of sulfuric acid to sodium bisulfate or alkali metal bisulfate, when an alkali metal hydroxide or oxide other than sodium hydroxide is used, and not converting the organic acids to unstable salts which revert back to the acids in the bottom portion of splitter (4). Analysis of the stream in line (16) from the bottom of tar cracking during the periods of operation of Example 1 and comparative Examples 1A and 1B confirm the low levels of corrosion in other down stream equipment and the minimization of toxic heavy metals in this primary waste stream from the process. The difference between 3 ppm by weight of chromium in the phenol tar waste stream and the lowest level achieved following the best prior art practice which is 5 ppm constitutes a 40% by weight reduction in chromium content in this waste stream. Such a reduction allows the phenol tar waste stream to be incinerated at a 40% higher rate and remain within government imposed environmental limits a level of about 4 ppm by weight chromium gives a 25% higher rate of incineration. This speeds disposition of this stream and increases process capacity. The range of the results of these analyses by weight are shown in Table 1A.

TABLE 1A

|  | Example 1 | Comparative 1A | Examples 1B |
| --- | --- | --- | --- |
| Neutralizer (2) pH Analysis of Bottoms Stream in line (16) | 4.2–4.7 | 6.0–6.5 | 3.8–3.9 |
| Chromium (parts per million) | 0–3 | 5–15 | 8–20 |
| Total Solids (parts per million) | 1200 | 5000 | 1100 |

Examples 2–5

By adding through line (27) an effective amount of aromatic hydrocarbons to the input stream in line (3) to the neutralizer (2), operated at a pH of from 4.0 to about 4.9, separation of the aqueous and organic phases is greatly enhanced and the level of sodium salts in the organic phase leaving the neutralizer (2) through line (5) is surprisingly reduced. The reduction in sodium salts in the organic phase leaving neutralizer (2) through line (5) also reduces the total solids or ash content in the waste stream leaving tar cracking (14) through line (16). The effect of added aromatic hydrocarbons on sodium salt content in the organic phase and on total solids in the tar cracking waste steam is illustrated in Table 2. All quantities are based upon weight.

TABLE 2

| Examples | 2 | 3 | 4 | 5 |
| --- | --- | --- | --- | --- |
| % Aromatic Hydrocarbons added through line 27 to Cleavage Mass in line (3) | 0 | 3 | 5 | 10 |
| Parts per Million Sodium in Stream in line (5) | 200 | 150 | 80 | 55 |
| Parts per Million Total Solids in Stream in line (16) | 1500 | 1400 | 800 | 800 |
| Parts per Million Chromium in Stream in line (16) | 3.0 | — | 2.4 | — |

In Examples 2–5 the phenol process was conducted as set forth in Example 1 except that there was added to the cleavage mass in line (3) the percent by weight of aromatic hydrocarbons through line (27) set forth in Table 2. The level of sodium salts in the stream in line (5) by analysis for sodium and the level of total solids in the stream in line (16) were monitored. The composition of the added aromatic hydrocarbons was as follows:

| Cumene | 77–89% |
| --- | --- |
| Alpha-methyl styrene | 10–20% |
| Other | 1–3% |

These results show that even a small amount of added aromatic hydrocarbons around 3%, significantly reduced the sodium salt level in the organic phase when the pH of neutralizer (2) maintained in the range of 4.0 to about 4.9. When the level of added aromatic hydrocarbons is in the range of from about 5% to about 10%, there is a further significant reduction of sodium salt level in the organic phase as well as a substantial reduction in total solids in the waste stream from the tar cracking operation.

All patents cited herein are expressly incorporated in this specification by reference and are a part of the teaching of this invention.

Unless expressly stated otherwise, all parts, percents or other expressions of quantity are based upon weight.

Although in the description of the present invention, sodium hydroxide, which is the alkali metal hydroxide most widely used in commercial manufacture of phenol, has been indicated as the agent to neutralize the residual acid in the cleavage mass, the skilled artisan will recognize that any alkali metal oxide or hydroxide can be used in the practice of the invention since the close control in the neutralizing equipment of pH in the range of 4.0 to about 4.9 is the key to the invention not the particular alkali metal hydroxide used to control pH in this range.

We claim:

1. An improved method for the recovery of phenol from a cleavage mass resulting from the sulfuric acid cleavage of cumene hydroperoxide comprising neutralizing the cleavage mass, forming an aqueous phase and an organic phase, separating the organic phase into an acetone-rich stream and a phenol-rich stream removing phenol tars from the phenol-rich stream and cracking the phenol tars wherein the improvement comprises maintaining the pH of the cleavage mass during neutralization between 4.0 and about 4.9 whereby the sulfuric acid is converted to the bisulfate salt and substantially no free sulfuric acid remains in the cleavage mass and corrosion of process equipment is reduced.

2. The method of claim 1 wherein the method further comprises purifying the acetone-rich stream and wherein the improvement further comprises raising the pH of the acetone-rich stream to about 9 after the stream is separated from the phenol-rich stream but before the acetone-rich stream is purified whereby organic acids in the acetone-rich stream are neutralized before the stream is purified and the corrosion of processing equipment is further reduced.

3. The method of claim 1 wherein the pH of the cleavage mass in the neutralizer is between 4.0 and about 4.7.

4. The method of claim 1 wherein the pH of the cleavage mass in the neutralizer is between 4.0 and about 4.5.

5. The method of claim 1 wherein the pH of the cleavage mass in the neutralizer is between 4.0 to about 4.2.

6. The method of claim 1 wherein the improvement further comprises adding to the cleavage mass before it is neutralized aromatic hydrocarbons in an amount of from about 3% to about 15% by weight of the cleavage mass whereby the separation of the organic and aqueous phases is enhanced and the level of salts in the organic phase is reduced.

7. The method of claim 1 wherein the improvement further comprises removing from the organic phase substantially all of the entrained water visible as a faint haze before the organic phase is separated into an acetone rich stream and a phenol-rich stream whereby the level of sodium salts in the phenol-rich stream and the phenol tars is substantially reduced.

8. A phenol tar waste composition produced by cleaving cumene hydroperoxide to produce a cleavage mass, neutralizing the cleavage mass at a pH of from 4.0 to about 4.9, forming an aqueous phase and an organic phase, separating the organic phase into an acetone-rich stream and a phenol-rich stream, removing phenol tars from the phenol-rich stream, cracking the phenol tars and removing from the cracked phenol tars a phenol tar waste composition wherein the phenol tar waste composition comprises no more than about 4 parts per million by weight of chromium whereby the phenol tar waste composition can be disposed of by incineration in compliance with government imposed environmental elements at about a 25% increased rate of incineration.

9. The phenol tar waste composition of claim 8 which comprises no more than about 3 parts per million by weight of chromium.

* * * * *